(12) United States Patent
Biller et al.

(10) Patent No.: US 6,624,334 B1
(45) Date of Patent: Sep. 23, 2003

(54) METHOD FOR PRODUCTION OF ARYL ALKYL ETHERS

(75) Inventors: Efim Biller, Vienna (AT); Edgar Fuhrmann, Castrop-Rauxel (DE); Detlef Hagena, Höxter (DE); Heinz Günter Janneck, Datteln (DE); Jörg Talbiersky, Dorsten (DE); Lutz Walther, Holzminden (DE)

(73) Assignees: Haarmann & Reimer GmbH (DE); Bayer Aktiengesellschaft (DE)

( * ) Notice: Subject to any disclaimer, the term of this patent is extended or adjusted under 35 U.S.C. 154(b) by 0 days.

(21) Appl. No.: 10/110,011

(22) PCT Filed: Oct. 4, 2000

(86) PCT No.: PCT/EP00/09699

§ 371 (c)(1),
(2), (4) Date: Apr. 8, 2002

(87) PCT Pub. No.: WO01/27060

PCT Pub. Date: Apr. 19, 2001

(30) Foreign Application Priority Data

Oct. 13, 1999 (DE) .......................... 199 49 319

(51) Int. Cl.$^7$ .......................... C07C 41/00; C07C 43/02
(52) U.S. Cl. .......................... 568/630; 568/632; 568/650; 568/658
(58) Field of Search .............................. 568/630, 632, 568/650, 658

(56) References Cited

U.S. PATENT DOCUMENTS 3,911,022 A * 10/1975 McCloud et al. ........... 568/630
4,487,975 A * 12/1984 Ratton .................... 558/423

* cited by examiner

*Primary Examiner*—Samuel Barts
*Assistant Examiner*—Sikarl A. Witherspoon
(74) *Attorney, Agent, or Firm*—Pendorf & Cutliff

(57) ABSTRACT

Aryl alkyl ethers can be produced by the reaction of hydroxyaromatics with an alcohol in the presence of a catalyst. This process achieves higher yields of aryl alkyl ethers and the formation of ring-alkylated products and dialkyl ethers is markedly reduced.

6 Claims, No Drawings

METHOD FOR PRODUCTION OF ARYL ALKYL ETHERS

This application is a 371 of PCT/EP00/09699, filed Oct. 4, 2000, and published as WO 01/27060 on Apr. 19, 2001.

FIELD OF THE INVENTION

The invention relates to a process for the preparation of aryl alkyl ethers in which hydroxyaromatics are reacted with an alcohol in the presence of a catalyst.

Aryl alkyl ethers, such as anisole (methyl phenyl ether), are required, for example, inter alia as intermediates in the syntheses of medicaments and fragrances/flavorings.

BACKGROUND OF THE INVENTION

EP 076 221 A1 describes the etherification of hydroxyaromatics with alcohols in the presence of a carboxylic acid salt and a metal halide.

A further process of this type is described in JP-4345852, which is carried out in the form of a batch process. In this process, over the course of the ten-hour reaction at 240° C. in an autoclave, the product concentration increases to 20.6% after 1 hour, and to 93% after 10 hours. The reaction is carried out at 180 to 280° C., preferably at approximately 240° C., where alcohols are preferably used in an at least identical quantitative amount as the phenols. The catalyst is used in the examples in an amount of approximately 1.75 parts by weight per 1 part by weight of phenol. After a reaction period of two hours, the anisole yield is approximately 42.6% and, following reaction for ten hours and a large excess of methanol, can be increased to approximately 87%.

A disadvantage of this process, in particular in the case of the high excess of alcohol which is required to increase the yield, is the undesired formation of ring-alkylated products, and of dialkyl ethers. In addition, the catalyst concentration used is so high that it is not possible to achieve a homogeneous solution either in the starting mixture or in the catalyst at atmospheric pressure. This two-phase mixture with a salt component cannot be used for a continuous reaction procedure. In addition, prior to the distillation, a further process step to separate off the salt is required, which involves a filtration and extraction.

SUMMARY OF THE INVENTION

The object of the invention was therefore to provide a process for the preparation of aryl alkyl ethers in which significantly higher yields are achieved and the formation of ring-alkylated products and dialkyl ethers is markedly reduced.

This object is achieved by a process of the preparation of aryl alkyl ethers in which a hydroxyaromatic is reacted with an alcohol in the presence of a catalyst, where a mixture comprising a hydroxyaromatic which is homogeneous at atmospheric temperature, alcohol and catalyst is introduced into the reactor, reacted at a temperature of from approximately 250 to approximately 370° C. and the product concentration in the reaction mixture is set such that the catalyst does not precipitate out.

DETAILED DESCRIPTION OF THE INVENTION

Compared with the generic process of JP 4345852, according to the invention an increase in the space/time yield by approximately a factor of 3 is achieved in the case of a batch mixture, and by a factor of >9 in the case of a continuous process. Although reaction at relatively high temperatures usually leads to an increased yield of ring-alkylated compounds, this is not the case in the process according to the invention. Surprisingly, the selectivity of the process according to the invention is increased such that there is virtually no formation of dialkyl ethers. Moreover, the catalyst in the reaction mixture does not have a detrimental effect on the subsequent distillation.

Hydroxyaromatics which can be used according to the invention are those of the general formula $HO-Ar-(R)_n$, in which Ar is a substituted or unsubstituted benzene ring or substituted or unsubstituted aromatic ring system such as naphthalene anthracene or phenanthrene; the substituents R or the substituent R are identical or different and is/are a hydroxyl group, a straight-chain or branched alkyl radical or alkenyl radical having 1 to 6 carbon atoms, an optionally substituted phenyl radical, an optionally substituted cycloalkyl radical, a phenyl alkyl radical whose alkyl radical contains 1 to 4 carbon atoms, and n is an integer from 1 to 5. Particular preference is given, for example, to phenol, p-cresol, xylenol, 2-naphthol, pyrocatechol, resorcinol and hydroquinone. It must also be emphasized that the alkyl groups on hydroxyaromatics have entirely immobile behavior under the reaction conditions described.

Alcohols to be used in the process according to the invention are primary, secondary and tertiary alcohols, such as methanol, ethanol, n-propanol, isopropanol, the butanols, 1-butanol, 2-butanol, tert-butanol, n-pentanol and its branched isomers and benzyl alcohols.

The molar ratio of hydroxyaromatic to alcohol can preferably be set to approximately 0.5:1, in particular approximately 1:1.

Catalysts which are suitable according to the invention are aromatic carboxylic acids, such as benzoic acid and phthalic acid and alkylated derivatives thereof and aliphatic carboxylic acids, such as acetic acid, propionic acid and substituted fatty acids and salts thereof. Substituted fatty acids are, for example, those having 8 to 20 carbon atoms. Also suitable are arylalkylcarboxylic acids, such as phenylbenzoic acid. Counterions are, for example, alkali metals and alkaline earth metals, preferably sodium, potassium, lithium, calcium, magnesium and barium.

The catalyst concentration can preferably be set such that the molar ratio of catalyst to hydroxyaromatic is preferably approximately $\leq 1:30$, in particular 1:32 to 1:60, for example also 1:40.

The process according to the invention can be carried out as a batch process or continuously, preference being given to the continuous process procedure. It has been observed that in the case of the continuous procedure, the volume is very much better utilized because, compared with the batch process, particularly when methanol is used, its concentration in the liquid phase is very much higher than in the gas phase.

The process is preferably carried out in a tubular reactor. The mixture fed into the reactor is a homogeneous solution at atmospheric pressure. The temperature in the reactor at which the reaction is carried out can be approximately 250 to 370° C, preferably at least approximately 275° C.

The residence time of the starting compounds or of the product in the reactor is regulated by the amount of starting materials fed in. The feed amount is preferably set such that the catalyst does not precipitate out or such that a conversion of at most approximately 40% of reaction product, based on the weight of the alkyl aromatic used, is obtained. The conversion is preferably approximately 35 to 40% of product, based on the hydroxyaromatic. This procedure is therefore particularly advantageous because the product can still be distilled. This is advantageous over the known processes since at this point in the process procedure it is not necessary to separate off the catalyst; instead, distillation can be carried out immediately. In addition, the space/time yield in the case of the continuous procedure is significantly improved compared with higher conversions.

The preparation of anisole is described below by way of example of the process according to the invention. The process procedure described here, however, also in principle applies to the preparation of other products obtainable by the process according to the invention.

The starting substances phenol, methanol and potassium benzoate are mixed to give a homogeneous solution, which is then pumped continuously through a tubular reactor with a volume of 1,520 ml. The starting mixture comprises, for example, 71.27% by mass of phenol, 24.26% by mass of methanol, 2.92% by mass of benzoic acid and 1.56% by mass of potassium hydroxide. The temperature in the reactor is 340° C., and the pressure is approximately 80 bar. During the reaction, dimethyl ether and carbon dioxide form as gaseous products in very small amounts; these are collected in a waste-gas trap and then combusted. The product concentration in the reactor is set at 40% by weight, based on the amount of phenol fed in. The mixture comprising the product taken from the reactor is sufficiently polar for the catalyst not to precipitate out. It is cooled to approximately 50° C., decompressed and collected in an intermediate container.

The catalyst is worked up using distillation. Firstly, the unreacted methanol is recovered. Then, an azeotrope of anisole and water is drawn off as top product. Following phase separation between anisole and water, the anisole is continuously returned to the distillation head. This operation is carried out until all of the water has been removed azeotropically. This gives, as the top product, an anhydrous anisole in a purity of 99.9%. After as much anisole as possible has been separated off, the distillation is ended. The homogeneous residue comprises all of the catalyst, unreacted phenol and traces of anisole. After being topped up with methanol and phenol, this solution is recycled in its entirety as a raw material for the preparation of anisole.

EXAMPLE 1

Preparation of 2-methoxynaphthalene (nerolin)

The starting substances 2-naphthol, methanol and potassium benzoate are mixed to give a homogeneous solution which is then pumped continuously through a tubular reactor with a volume of 1520 ml. The starting mixture comprises 49.4% by mass of 2-naphthol, 49.3% by mass of methanol, 0.92% by mass of benzoic acid and 0.49% by mass of calcium hydroxide. The temperature in the reactor is 320° C., and the pressure is approximately 100 bar. The feed amount is set such that the residence time in the reactor is approximately 5 hours. The reactor product is cooled to approximately 60° C. in an aftercooler and then decompressed to ambient pressure.

Under the experimental conditions given above, a reaction product is obtained which comprises approximately 35.5% by mass of 2-methoxynaphthalene. In addition, it comprises unreacted methanol, 2-naphthol, potassium benzoate and water of reaction from the etherification. Comparable with the anisole preparation, the catalyst is worked up by distillation. Firstly, the unreacted methanol is removed. Water is then drawn off and then a water-containing fore-run of 2-methoxynaphthalene, which can be reused for redistillation. The next fraction is a 2-methoxynaphthalene with a quality of at least 99% by mass. After as much of the 2-methoxynaphthalene as possible has been separated off, the distillation is ended.

The homogeneous residue comprises all of the catalyst, unreacted 2-naphthol and traces of 2-methoxynaphthalene. After being topped up with methanol and 2-naphthol, this solution is recycled in its entirety as a raw material for the preparation of 2-methoxynaphthalene.

EXAMPLE 2

Preparation of 4-methylanisole

The starting substances p-cresol, methanol and potassium benzoate are mixed, giving a homogeneous solution which is then pumped continuously through a tubular reactor with a volume of 1520 ml. The starting mixture comprises 73.7% by mass of p-cresol, 21.9% by mass of methanol, 2.9% by mass of benzoic acid and 1.55% by mass of potassium hydroxide. The temperature in the reactor is 340° C., and the pressure is approximately 80 bar. The feed amount is set such that the residence time in the reactor is approximately 5 hours. The reactor product is cooled to approximately 50° C. in an aftercooler and then decompressed to ambient pressure.

Under the experimental conditions given above, a reaction product is obtained which comprises approximately 36.3% by mass of 4-methyl anisole. In addition, it comprises unreacted methanol, p-cresol, potassium benzoate and water of reaction from the etherification. Comparable with the preparation of anisole, the catalyst is worked up by distillation. Firstly, the unreacted methanol is removed. Then, water is drawn off and then a water-containing pre-run of 4-methyl anisole, which can be reused for the redistillation. The next fraction is a 4-methyl anisole having a quality of at least 99% by mass. After as much of the 4-methyl anisole as possible has been separated off, the distillation is ended.

The homogenous residue comprises all of the catalyst, unreacted p-cresol and traces of 4-methyl anisole. After being topped up with methanol and p-cresol, this solution is recycled in its entirety as a raw material for the preparation of 4-methylanisole.

What is claimed is:
1. A process for the preparation of aryl alkye ethers comprising the step of reacting a hydroxyaromatic with an alcohol in the presence of a catalyst to form a mixture, wherein the mixture is homogenous, at atmospheric pressure and is introduced into a reactor and reacted at a temperature of from about 250 to about 370° C., and wherein the catalyst does not precipitate out, wherein the process is a continuous process, wherein the ratio of catalyst to hydroxyaromatic is greater than 0 and $\leq$1:30.

2. The process as claimed in claim 1, wherein the molar ratio of hydroxyaromatic to alcohol is about 0.5:1.

3. The process as claimed in claim 1, wherein the ratio of catalyst to hydroxyaromatic is approximately 1:32 to 1:60.

4. The process as claimed in claim 3 wherein the ratio of catalyst to hydroxyaromatic is approximately 1:40.

5. The process as claimed in claim 1, wherein the hydroxyaromatic is selected from the group consisting of phenol, p-cresol, 2-naphthol, resorcinol, pyrocatechol and hydroquinone.

6. The process as claimed in claim 1, wherein the alcohol is selected from the group consisting of methanol, ethanol, isopropanol, butanol, tert-butanol, propanol, pentanol and benzyl alcohol.

* * * * *

UNITED STATES PATENT AND TRADEMARK OFFICE
CERTIFICATE OF CORRECTION

PATENT NO. : 6,624,334 B1
DATED : September 23, 2003
INVENTOR(S) : Biller et al.

It is certified that error appears in the above-identified patent and that said Letters Patent is hereby corrected as shown below:

Column 4,
Line 64, should read as -- aryl alkyl ethers --
Line 67, should read as -- wherein the mixture is homogenous at atmospheric pressure --

Signed and Sealed this

Twenty-second Day of June, 2004

JON W. DUDAS
*Acting Director of the United States Patent and Trademark Office*